United States Patent [19]

Rose et al.

[11] 4,213,758
[45] Jul. 22, 1980

[54] OXIDATION HAIR DYES BASED UPON TETRAAMINOPYRIMIDINE DEVELOPERS AND COUPLERS THEREFOR

[75] Inventors: David Rose, Hilden; Erwin Weinrich, Haan; Edgar Lieske, Düsseldorf, all of Fed. Rep. of Germany

[73] Assignee: Henkel Kommanditgesellschaft auf Aktien, Düsseldorf-Holthausen, Fed. Rep. of Germany

[21] Appl. No.: 868,304

[22] Filed: Jan. 10, 1978

[30] Foreign Application Priority Data

Jan. 20, 1977 [DE] Fed. Rep. of Germany ....... 2702118

[51] Int. Cl.$^2$ ................................................. A61K 7/13
[52] U.S. Cl. ................................................. 8/409; 8/421
[58] Field of Search ............................ 8/10.2, 11, 32

[56] References Cited

U.S. PATENT DOCUMENTS

| | | | |
|---|---|---|---|
| 3,134,721 | 5/1964 | Seemuller | 8/10.2 |
| 3,184,387 | 5/1965 | Seemuller | 8/10.2 |
| 3,415,608 | 12/1968 | Tucker | 8/10.2 |
| 3,488,138 | 1/1970 | Iscowitz | 8/10.2 X |
| 3,712,790 | 1/1973 | Kalopissis et al. | 8/10.2 |
| 4,003,699 | 1/1977 | Rose et al. | 8/10.2 |

Primary Examiner—Norman Morgenstern
Assistant Examiner—Vera C. Clarke
Attorney, Agent, or Firm—Hammond & Littell, Weissenberger and Muserlian

[57] ABSTRACT

An aqueous hair dye preparation comprising an oxidation dyestuff combination of a developer component consisting of a tetraaminopyrimidine derivative or a water-soluble acid addition salt thereof and as coupler, at least one of the following:

(a) 2,4-diaminophenol
(b) 2,4-diamino-3-chlorophenol
(c) 2-amino-4-methylphenol
(d) 3-amino-2,6-dimethylphenol
(e) 2,2',4,4'-tetrahydroxybenzophenone
(f) 2,4-diamino-6-methylphenol
(g) 3,4-diaminophenetole
(h) 1,3-dihydroxy-5-methylaminobenzene
(i) 1-hydroxy-7-aminonaphthalene
(j) 1-hydroxy-8-aminonaphthalene
(k) 1,6-dihydroxynaphthalene
(l) 2,7-dihydroxynaphthalene
(m) 3,5-dimethoxyphenol, as well as a process for dyeing hair by utilizing this oxidation dyestuff combination.

9 Claims, No Drawings

OXIDATION HAIR DYES BASED UPON TETRAAMINOPYRIMIDINE DEVELOPERS AND COUPLERS THEREFOR

THE PRIOR ART

Of great importance for the dyeing of hair are the so-called oxidation dyestuffs because of their intensive colors and very good fastness. These dyestuffs are formed by the oxidative coupling of a developer component with a coupling component. The developers customarily used are nitrogenous bases, such as p-phenylenediamine derivatives, diaminopyridines, 4-aminopyrazolone derivatives or heterocyclic hydrazones. Useful as so-called coupling components are m-phenylenediamine derivatives, phenols, naphthols, resorcinol derivatives and pyrazolones.

Good oxidation dyestuff components for hair dyeing must fulfill all of the following requirements.

They have to be able to develop a sufficient intensity of the desired color shades when oxidatively coupled with the respective developer component or coupling component. Furthermore, they have to possess a capacity for being absorbed by human hair, which capacity ranges from sufficient to very good; and in addition, they should be unobjectionable from toxicological and dermatological viewpoints.

As developers, it is customary to use the class of compounds consisting of substituted or unsubstituted p-phenylenediamines. However, this class of compounds has the disadvantage that sensitivity reactions and subsequently severe allergies are caused in numerous persons. The developers which have been recently proposed for avoiding these dermatological disadvantages are not always fully satisfactory with respect to their technical application.

U.S. Pat. No. 4,003,699, Jan. 18, 1977, discloses oxidation hair dyes based upon tetraaminopyrimidine developers which can react with the known couplers generally used in oxidation hair dyestuffs to give very intensive, varying shades which previously could not be obtained with these known couplers. U.S. Pat. No. 4,003,699 also discloses the special usefulness of its tetraaminopyrimidines employed as developers in combination with certain m-aminophenols as blue-coupling components.

It is further disclosed in the above patent that the tetraaminopyrimidines disclosed therein are characterized by very good fastness of the dyeings produced with them, good water-solubility, good storage stability, and toxicological and dermatological harmlessness.

Among the various tints producable by oxidation hair dyes, great importance is attached to the intensive yellow and yellowish-brown tints and some special shades. The coupler components normally used as red and yellow coupler components and for special tints have not produced satisfactory results when combined with the tetraaminopyrimidines which otherwise give very satisfactory results when used as developer components. Thus, the task arose of providing coupler components which, when combined with the tetraaminopyrimidines used as developer substances, produce intensive yellow, yellowish-brown, brown and special tints which meet all requirements with respect to fastness, stability and toxicological and dermatological harmlessness desirable in oxidation hair dyes.

OBJECTS OF THE INVENTION

An object of the invention is to provide usable oxidation hair dyes containing suitable components which optimally satisfy the above requirements.

Another object of the present invention is to provide an oxidation dyestuff combination of a developer component and a coupling component, which is based on tetraaminopyrimidines as the developer component and certain aromatic compounds as the coupler component.

These and further objects of the present invention will become apparent as the description thereof proceeds.

DESCRIPTION OF THE INVENTION

The present invention provides a composition and process for dyeing hair based upon an oxidation dyestuff combination of a developer component which is a tetraaminopyrimidine and a coupling component therefor. It has now been found that the above-specified requirements can be fulfilled to an especially significant extent by the use of hair coloring preparations that are based on oxidation dyestuff combinations containing tetraaminopyrimidines of the formula

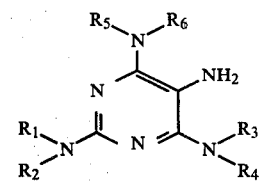

and their inorganic or organic water-soluble acid addition salts as developers, in which $R_1$ to $R_6$ are each selected from the group consisting of hydrogen, alkyl having 1 to 4 carbon atoms, aryl, substituted aryl, and $-(CH_2)_n-X$, in which n is an integer from 1 to 4, and X is selected from the group consisting of hydroxy, halogen and $-NR_7R_8$ wherein $R_7$ and $R_8$ are selected from the group consisting of hydrogen and alkyl having 1 to 4 carbon atoms and can form with the nitrogen atom a heterocyclic ring which may contain one additional nitrogen atom or an oxygen atom, and in which $R_1$ to $R_6$, together with the respective nitrogen atom, likewise can designate an optionally substituted five-membered or six-membered heterocyclic ring containing one or two nitrogen atoms, or one nitrogen atom and one oxygen atom, and containing at least one coupling component selected from the group consisting of (a) 2,4-diaminophenol
(b) 2,4-diamino-3-chlorophenol
(c) 2-amino-4-methylphenol
(d) 3-amino-2,6-dimethylphenol
(e) 2,2',4,4'-tetrahydroxybenzophenone
(f) 2,4-diamino-6-methylphenol
(g) 3,4-diaminophenetole
(h) 1,3-dihydroxy-5-methylaminobenzene
(i) 1-hydroxy-7-aminonaphthalene
(j) 1-hydroxy-8-aminonaphthalene
(k) 1,6-dihydroxynaphthalene
(l) 2,7-dihydroxynaphthalene
(m) 3,5-dimethoxyphenol.

More particularly, the present invention is directed to an aqueous preparation for the dyeing of hair consisting essentially of (1) from 0.2% to 5% by weight of an oxidation dyestuff combination of a developer component, and a coupling component in substantially equimolar amounts, said developer component consisting essentially of (A) a tetraaminopyrimidine of the formula

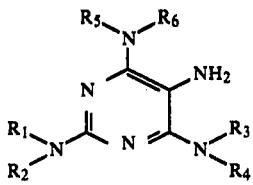

wherein $R_1$, $R_2$, $R_3$, $R_4$, $R_5$ and $R_6$ are each selected from the group consisting of hydrogen, phenyl, alkyl having 1 to 4 carbon atoms, phenylalkyl having 7 to 10 carbon atoms, phenylalkenyl having 7 to 10 carbon atoms, $$X-(CH_2)_n-$$

wherein n is an integer from 1 to 4, and X is selected from the group consisting of hydroxyl, halogen and $NR_7R_8$— in which $R_7$ and $R_8$ are each hydrogen or alkyl having 1 to 4 carbon atoms, and together with the nitrogen atom $R_7$ and $R_8$ form a member selected from the group consisting of a 5 to 6 membered heterocyclic ring optionally containing an additional nitrogen atom or oxygen atom, and wherein $R_1$ and $R_2$, or $R_3$ and $R_4$, or $R_5$ and $R_6$, together with the nitrogen atom form a five to six membered heterocyclic ring optionally containing another nitrogen or oxygen atom in the ring and (B) a water-soluble acid addition salt of (A), and said coupler component consisting essentially of at least one compound selected from the group consisting of
(a) 2,4-diaminophenol
(b) 2,4-diamino-3-chlorophenol
(c) 2-amino-4-methylphenol
(d) 3-amino-2,6-dimethylphenol
(e) 2,2',4,4'-tetrahydroxybenzophenone
(f) 2,4-diamino-6-methylphenol
(g) 3,4-diaminophenetole
(h) 1,3-dihydroxy-5-methylaminobenzene
(i) 1-hydroxy-7-aminonaphthalene
(j) 1-hydroxy-8-aminonaphthalene
(k) 1,6-dihydroxynaphthalene
(l) 2,7-dihydroxynaphthalene
(m) 3,5-dimethoxyphenol;
(2) from 0% to 5% by weight of a direct dyestuff; (3) 0% to 30% by weight of a surfactant; (4) from 0% to 25% by weight of thickeners; and (5) the balance up to 100% by weight of water.

A particularly preferred subgenus of the above-mentioned developer component is wherein $R_1$, $R_2$, $R_3$, $R_4$, $R_5$ and $R_6$ are each selected from the group consisting of hydrogen, methyl, ethyl, isopropyl, n-propyl, butyl, phenyl, benzyl and benzylidene, or $-(CH_2)_n-X$, and wherein $R_1$ and $R_2$, or $R_3$ and $R_4$, or $R_5$ and $R_6$, together with the nitrogen atom form a substituent selected from the group consisting of piperidino and morpholino; and wherein n is 1, 2 or 3 and X is selected from the group consisting of hydroxyl, halogen and $-NR_7R_8$ in which $R_7$ and $R_8$ are each hydrogen or alkyl having 1 to 4 carbon atoms.

The above tetraaminopyrimidines are disclosed in U.S. Pat. No. 4,003,699, the teachings of which are incorporated herein by reference.

The tetraaminopyrimidines which are to be used as developer components according to the invention can be used either as such or in form of their water-soluble acid addition salts with non-toxic inorganic acids or organic acids, such as for example, hydrochloric acid, sulfuric acid, phosphoric acid, acetic acid, propionic acid, lactic acid or citric acid.

The preparation of most tetraaminopyrimidines to be used as developer components according to the invention is already known in the literature and can be taken from the monograph by D. J. Brown, in the series "Heterocyclic Compounds", Interscience Publishers, 1962, Vols. I and II, "The Pyrimidines". The preparation of some of the tetraaminopyrimidines of the invention is disclosed in U.S. Pat. No. 4,003,699.

To synthesize the tetraaminopyrimidine compounds to be used according to the invention, the starting material generally is a 2,4,6-aminopyrimidine, into which the 5-amino group is introduced by nitrosation and subsequent reduction. It is also possible to start from the correspondingly substituted triaminoalkylmercaptopyrimides and to replace the alkylmercapto group with an amino group. The latter method is especially suitable for the introduction of substituted amino groups into the 2-, 4-, or 6-positions of the pyrimidine ring.

Suitable examples of developer components to be used according to the invention, are for example: 2,4,5,6-tetraamino-pyrimidine, 4,5-diamino-2,6-bis(methylamino)-pyrimidine, 2,5-diamino-4,6-bis-(methylamino)-pyrimidine, 4,5-diamino-6-(butylamino)-2-(dimethylamino)-pyrimidine, 2,5-diamino-4-(diethylamino)-6-(methylamino)-pyrimidine, 4,5-diamino-6-(diethylamino)-(2-dimethylamino)-pyrimidine, 4,5-diamino-2-(diethylamino)-6-(methylamino)-pyrimidine, 4,5-diamino-2-(dimethylamino)-6-(ethylamino)-pyrimidine, 4,5-diamino-2-(dimethylamino)-6-(isopropylamino)-pyrimidine, 4,5-diamino-2-(dimethylamino)-6-(methylamino)-pyrimidine, 4,5-diamino-6-(dimethylamino)-2-(methylamino)-pyrimidine, 4,5-diamino-2-(dimethylamino)-6-(propylamino)-pyrimidine, 2,4,5-triamino-6-(dimethylamino)-pyrimidine, 4,5,6-triamino-2-(dimethylamino)-pyrimidine, 2,4,5-triamino-6-(methylamino)-pyrimidine, 4,5,6-triamino-2-(methylamino)pyrimidine, 4,5-diamino-2-(dimethylamino)-6-piperidinopyrimidine, 4,5-diamino-6-(methylamino)-2-piperidino-pyrimidine, 2,4,5-triamino-6-piperidino-pyrimidine, 2,4,5-triamino-6-anilino-pyrimidine, 2,4,5-triamino-6-(benzylamino)-pyrimidine, 2,4,5-triamino-6-(benzylideneamino)-pyrimidine, 4,5,6-triamino-2-piperidino-pyrimidine, 5-amino-2,4,6-tris-(methylamino)pyrimidine, 2,4,5-triamino-6-(di-n-propylamino)pyrimidine, 2,4,5-triamino-6-morpholino-pyrimidine, 2,5,6-triamino-4-(dimethylamino)-pyrimidine, 4,5,6-triamino-2-morpholino-pyrimidine, 2,4,5-triamino-6-(β-hydroxyethyl-amino) pyrimidine, 4,5,6-triamino-2-[(β-aminoethyl)amino]-pyrimidine, 2,5,6-triamino-4-[(β-methylamino)-ethylamino]-pyrimidine, 2,5-diamino-4,6-[(bis-γ-diethylamino)-propylamino]-pyrimidine, 4,5-diamino-6-[β-hydroxyethyl)-amino]-2-(methylamino)pyrimidine, 5-amino-2,4,6-(triethylamino)-pyrimidine, and 5-amino-6-anilino-2,4-[bis-(β-hydroxyethyl)-amino]-pyrimidine.

The coupler components that can be used according to the present invention are compounds known in the literature and are commercially available products.

In the hair coloring preparations according to the invention, the coupler substances are generally used in substantially equimolar amounts, relative to the developer substances used. Although an equimolar amount is preferred, it is possible to use more or less of either component in a certain excess or deficiency, as for example the molar range of 2:1 to 1:2, more preferably up to a 10% excess or deficiency.

Furthermore, the developer component and the coupling component may be used as pure ingredients or as mixtures. Not only can the developer component consist of mixtures of the tetraaminopyrimidines to be used according to the invention, but the coupler substance can also consist of mixtures of the above-mentioned compounds.

In addition, the hair coloring preparations according to the invention can contain admixtures of other customary developing components. Besides developer and/or coupler components they, if necessary, also contain the customary direct dyestuffs in case the latter are needed for obtaining certain shades. From 0% to 5% direct dyestuffs may be employed.

As in the case of other oxidation hair dyes, the oxidative coupling, i.e., the developing of the dye, can in principle be effected by atmospheric oxygen. However, it is advantageous to use chemical oxidizing agents. Suitable examples are especially hydrogen peroxide or its products of addition to urea, melamine and sodium borate, as well as mixtures of such hydrogen peroxide addition products with potassium peroxydisulfate.

As developer components the tetraaminopyrimidines according to the invention have the advantage that they readily yield fully satisfactory hair dyeing results in oxidative coupling with atmospheric oxygen. Thus hair damage by the oxidizing agents, otherwise used in oxidative coupling, can be avoided. But if a brightening or bleaching effect is desired in the hair, in addition to the coloring effect, then the concurrent use of chemical oxidizing agents is necessary.

In their use, the hair dyes according to the invention are incorporated into suitable aqueous cosmetic preparations, such as creams, emulsions, gels or simple solutions and immediately before application to the hair, one of the above-mentioned oxidizing agents is added. These hair dyeing compositions contain coupling and developing components in amounts of from 0.2% to 5% by weight, preferably from 1% to 3% by weight.

For the preparation of creams, emulsions or gels, the dye components are mixed with the additional ingredients customarily used in such preparations. Such additional ingredients are, for example, wetting agents or emulsifiers of the anionic or nonionic type, such as alkybenzenesulfonates, higher fatty alcohol sulfates, higher alkylsulfonates, higher fatty acid alkanolamides, addition products of ethylene oxide on higher fatty alcohols, thickeners, such as methyl cellulose, starch, higher fatty alcohols, paraffin oil and higher fatty acids. Furthermore, perfumes and hair-conditioning and grooming agents, such as pantothenic acid and cholesterol may be included.

Effective amounts of the above-mentioned additives are those customarily employed for this purpose. For example, effective amounts of wetting agents and emulsifiers range from 0.5% to 30% by weight, preferably from 1% to 15% by weight; and for thickeners, an effective amount ranges from 0.1% to 25% by weight, preferably from 1% to 15% by weight, based in each case on the total weight of the preparation. As a lower limit for the above additives, a zero percent lower limit is possible, if none of the additive is utilized.

The hair coloring preparations according to the invention can be applied in a weakly acid medium, a neutral medium or especially in an alkaline medium, preferably at a pH of 8 to 10, regardless of whether a solution, an emulsion, a cream, or a gel is employed.

These preparations are applied at a temperature which usually ranges from 15° C. to 40° C. and preferably is room temperature.

After the preparation has been allowed to react for about 30 minutes, the hair coloring preparation is removed from the hair to be dyed, by rinsing. Then the hair is washed with a mild shampoo, and finally is dried.

The compounds to be used in accordance with the invention as coupler components produce, when combined with the tetraaminopyrimidine developers, very intensive tints which are distinguished by particularly satisfactory lightfastness, a satisfactory penetrating capacity, and toxicological harmlessness.

The following examples are merely illustrative of the present invention without being deemed limitative in any manner thereof.

EXAMPLES

The following compounds were used as coupler components in the examples presented hereinafter:

| Coupler component: | |
|---|---|
| K 1 | 2,4-diaminophenol |
| K 2 | 2,4-diamino-3-chlorophenol |
| K 3 | 2-amino-4-methylphenol |
| K 4 | 3-amino-2,6-dimethylphenol |
| K 5 | 2,2',4,4'-tetrahydroxybenzophenone |
| K 6 | 2,4-diamino-6-methylphenol |
| K 7 | 3,4-diaminophenetole |
| K 8 | 1,3-dihydroxy-5-methylaminobenzene |
| K 9 | 1-hydroxy-7-aminonaphthalene |
| K 10 | 1-hydroxy-8-aminonaphthalene |
| K 11 | 1,6-dihydroxynaphthalene |
| K 12 | 2,7-dihydroxynaphthalene |
| K 13 | 3,5-dimethoxyphenol |

The following compound was used as a developer component in the examples presented hereinafter:
E 1: 2,4,5,6-tetraaminopyrimidine

EXAMPLE 1

The hair dyes according to the invention were used in the form of a cream emulsion. 0.01 mole of 2,4,5,6-tetraaminopyrimidine and 0.01 mole of the coupler components listed in the following Table were in each case incorporated into an emulsion containing 10 parts by weight of fatty alcohols having 12 to 18 carbon atoms,
10 parts by weight of fatty alcohol sulfate (sodium salt) having 12 to 18 carbon atoms, and
75 parts by weight of water.

The pH value of the emulsion was then adjusted to 9.5 by means of ammonia, and the emulsion was made up to 100 parts by weight with water. Oxidative coupling was effected with a 1% hydrogen peroxide solution acting as an oxidation agent, 10 parts by weight of the hydrogen peroxide solution being added to 100 parts by weight of the emulsion. The particular dyeing cream, with additional oxidation agent, was applied to human hair which was 90% grey and which had not been specially pretreated, and the cream was left on the hair for 30 minutes. After the dyeing process was completed, the hair was washed out with a conventional shampoo and subsequently dried. The colors obtained are given in the following Table.

TABLE

| Example | (a) Developer | (b) Coupler | Shade obtained with 1% H$_2$O$_2$ solution |
|---|---|---|---|
| 1 | E 1 | K 1 | Medium Brown |
| 2 | E 1 | K 2 | Yellowish brown |
| 3 | E 1 | K 3 | Yellowish brown |
| 4 | E 1 | K 4 | Violet |
| 5 | E 1 | K 5 | Auburn |
| 6 | E 1 | K 6 | Yellowish brown |
| 7 | E 1 | K 7 | Olive yellow |
| 8 | E 1 | K 8 | Chestnut brown |
| 9 | E 1 | K 9 | Reddish brown |
| 10 | E 1 | K 10 | Greyish violet |
| 11 | E 1 | K 11 | Green |
| 12 | E 1 | K 12 | Yellowish brown |
| 13 | E 1 | K 13 | Olive yellow |

The above colors are to be contrasted with those reported in Table I of U.S. Pat. No. 4,003,699.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A composition of the developer-coupler type for the dyeing of hair, consisting essentially of, I. as developer, at least one tetraaminopyrimidine selected from the group consisting of (A) at least one tetraaminopyrimidine of the formula

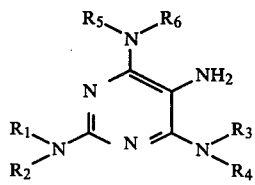

in which R$_1$, R$_2$, R$_3$, R$_4$, R$_5$ and R$_6$ are each selected from the group consisting of hydrogen, phenyl, alkyl having 1 to 4 carbon atoms, phenylalkyl having 7 to 10 carbon atoms, phenylalkenyl having 7 to 10 carbon atoms, X(CH$_2$)n— wherein n is an integer from 1 to 4, and X is selected from the group consisting of hydroxyl, halogen and NR$_7$R$_8$—in which R$_7$ and R$_8$ are each hydrogen or alkyl having 1 to 4 carbon atoms, and together with the nitrogen atom R$_7$ and R$_8$ form a member selected from the group consisting of a 5 to 6 membered heterocyclic ring optionally containing an additional nitrogen atom or oxygen atom, and wherein R$_1$ and R$_2$, or R$_2$ and R$_4$, or R$_5$ and R$_6$, together with the nitrogen atom form a five to six membered heterocyclic ring optionally containing another nitrogen or oxygen atom in the ring, and, (B) at least one water-soluble acid addition salt of (A), and, ·

II. as coupler, 2,4-diaminophenol, said developer and said coupler being present in the molar range of about 2:1 to 1:2.

2. The composition of claim 1, wherein the developer is a mixture of the tetraaminopyrimidines.

3. The composition of claim 1 which additionally contains conventional additives selected from the group consisting of conventional developers, and conventional couplers.

4. The composition of claim 1 wherein in the developer R$_1$, R$_2$, R$_3$, R$_4$, R$_5$ and R$_6$ are each selected from the group consisting of hydrogen, methyl, ethyl, isopropyl, n-propyl, butyl, phenyl, benzyl, benzylidene, and —(CH$_2$)$_n$—X, and wherein R$_1$ and R$_2$, or R$_3$ and R$_4$, or R$_5$ and R$_6$, together with the nitrogen atom form a substituent selected from the group consisting of piperidino and morpholino; and wherein n is 1, 2 or 3 and X is selected from the group consisting of hydroxyl, halogen and —NR$_7$R$_8$ in which R$_7$ and R$_8$ are each hydrogen or alkyl having 1 to 4 carbon atoms.

5. The composition of claim 1, wherein the developer is 2,4,5,6-tetraaminopyrimidine or a water-soluble acid addition salt thereof.

6. An aqueous preparation of the developer-coupler type for the dyeing of hair, consisting essentially of 0.2% to 5% by weight of the developer-coupler combination of claim 1; from 0% to 30% by weight of a surfactant; from 0% to 25% by weight of a thickener; and the remainder water.

7. The preparation of claim 6 which contains 1% to 3% by weight of the developer-coupler combination.

8. A process for the dyeing of hair comprising applying to said hair, at temperatures ranging substantially from 15° C. to 40° C. for a time sufficient to effect dyeing through oxidation, an effective amount of the developer-coupler composition according to claim 1 in an aqueous medium.

9. The process for the dyeing of hair of claim 8 wherein the oxidation is effected by the action of a chemical oxidizing agent.

* * * * *